United States Patent [19]

Kelly et al.

[11] Patent Number: 5,498,786
[45] Date of Patent: Mar. 12, 1996

US005498786A

[54] SYNTHESIS OF INTERMEDIATES IN THE PREPARATION OF ACAT INHIBITORS

[75] Inventors: Sarah E. Kelly, Mystic; George Chang, Ivoryton, both of Conn.

[73] Assignee: Pfizer Inc., New York, N.Y.

[21] Appl. No.: 117,109

[22] PCT Filed: Nov. 27, 1991

[86] PCT No.: PCT/US91/08758

§ 371 Date: Sep. 13, 1993

§ 102(e) Date: Sep. 13, 1993

[87] PCT Pub. No.: WO92/13843

PCT Pub. Date: Aug. 20, 1992

Related U.S. Application Data

[63] Continuation-in-part of Ser. No. 648,243, Jan. 31, 1991, abandoned.

[51] Int. Cl.$^6$ .................................................. C07C 231/00
[52] U.S. Cl. ............................ 554/67; 554/42; 554/68; 554/69; 554/101; 554/150; 554/154; 554/225; 554/229; 544/180; 544/235; 544/242; 544/253; 546/244
[58] Field of Search ........................... 554/154, 68, 69, 554/161, 225, 52, 150, 101, 51, 94, 88, 42, 67, 229; 546/168, 174, 298, 244; 544/180, 235, 242, 253

[56] References Cited

FOREIGN PATENT DOCUMENTS 0418071  3/1991  European Pat. Off. .
0459455  12/1991  European Pat. Off. .

OTHER PUBLICATIONS

Nohira et al, Chemicla Abstracts, vol. 110, No. 18, p. 653, 1989, 163720.
Sugai et al, Agricultural & Bio. Chem. vol. 54, No.12 1990, pp. 3337–3338.
Ogura et al, Bull. Chem. Soc. Jpn, vol. 55, No. 4, pp. 1216–1220, 1982.
Chemical Abstracts, vol. 85, No. 3, p. 65, 1976.
Nohira et al., "Optically–active 2–fluoroalkanoic acids and liquid crystal compositions containing them", 110 (18) Chemical Abstracts No. 163720, 653 (1989).
Petit et al.: "Stereoselective synthesis of optically active alpha–methyl esters", 31 (15) Tetrahedron Letters, 2149–2152 (1990).
Research Disclosure, "Process for the preparation of alkyl 2(–)arylsulfonyl Lactates", No. 306, 722–723 (New York, US), (1989).
Sugai et al.: "Lipase–catalyzed kinetic resolution of 2–hydroxyhexadecanoic acid and its esters", 54 (12) Agricultural and Biological Chemistry, 3337–3338 (1990).
Weinreb et al.: "A Mild, General Method for Conversion of Esters to Amides" 48 Tetrahedron Letters 4174–4174 (1977).
Kellogg et al.: "Synthesis of (Racemization Prone) Optically Active Thiols by $S_n2$ Substitution Using Cesium Thiocarboxylates", 51 J. Org. Chem., 3664–3671 (1986).
Owen et al.: "The Synthesis and Reduction of Optically Active 2–Mercaptopropionic Acid and Some Derivatives", (C) J. Chem. Soc., 2432–2440 (1971).
Effenberger et al.: "Racemisierungsfreie Substitution von 2–(Sulfonyloxy)carbonsäureestern mit Sauerstoff– und Schwefelnucleophilen", 119 Chem. Ber., 1594–1612 (1986).
Yamada et al.: "Stereochemical Studies. LII. Studies on the Stereochemical Courses in Deaminative Bromination of 3,5–Dichloro–L–tyrosine and in Amination of the Corresponding α–Bromo Acid. Existence of Strong Neighboring Phenoxide Group Participation", 26(1) Chem. Pharm. Bull., 178–184 (1978).
Kalaritis et al.: "Kinetic Resolution of 2–Substituted Esters Catalyzed by a Lipase Ex. Pseudomonas fluorescens", 55 J. Org. Chem., 812–815 (1990).
Ogura et al.: "A Convenient Method for Preparation of 2–(Methylthio)alkanoic Acids and Their Related Compounds Using the Carbanions of Substituted Malonic Esters", 55 Bull. Chem. Soc., 1216–1220 (1982).
Suter et al.: "A New Series of Testosterone Esters", 71 J.A.C.S. 3372–3374 (1949).

Primary Examiner—José G. Dees
Assistant Examiner—Deborah D. Carr
Attorney, Agent, or Firm—Peter C. Richardson; Paul H. Ginsburg; Garth Butterfield

[57] ABSTRACT

This invention relates to novel processes for synthesizing intermediates in the preparation of N-aryl and N-heteroarylamide inhibitors of the enzyme acyl coenzyme A: cholesterol acyltransferase (ACAT), and to novel intermediates used in such processes.

6 Claims, No Drawings

SYNTHESIS OF INTERMEDIATES IN THE PREPARATION OF ACAT INHIBITORS

This application is a continuation-in-part of U.S. application Ser. No. 648,243, filed Jan. 31, 1991, now abandoned.

BACKGROUND OF THE INVENTION

This invention relates to novel processes for synthesizing intermediates in the preparation of N-aryl and N-heteroarylamide inhibitors of the enzyme acyl coenzyme A: cholesterol acyltransferase (ACAT), and to novel intermediates used in such processes.

The foregoing ACAT inhibitors having synthetic intermediates which may be prepared by the processes of this invention are described and claimed in PCT Patent Application PCT/US 89/04033, entitled "New N-Aryl and N-Heteroarylamide and Urea Derivatives as Inhibitors of Acyl Coenzyme A: Cholesterol Acyl Transferase" and filed Sep. 15, 1989. They are also described and claimed in the United States continuation-in-part application 648677 claiming priority from such PCT application and filed on Mar. 21, 1991. The present application claims priority as a continuation-in-part of United States parent application 648243 filed on Jan. 31, 1991. These ACAT inhibitors are useful in the prevention of atherosclerosis, myocardial infarction and stroke.

Cholesterol that is consumed in the diet (dietary cholesterol) is absorbed as free cholesterol by the mucosal cells of the small intestine. It is then esterified by the enzyme ACAT, packaged into particles known as chylomicrons, and released into the bloodstream. Chylomicrons are particles into which dietary cholesterol is packaged and transported in the bloodstream. By inhibiting the action of ACAT, the ACAT inhibitors referred to above prevent intestinal absorption of dietary cholesterol and thus lower serum cholesterol levels. They are therefore useful in preventing atherosclerosis, heart attacks and strokes.

Also, by inhibiting the action of ACAT, the ACAT inhibitors referred to above enable cholesterol to be removed from the walls of blood vessels. This activity renders such compounds useful in slowing or reversing the development of atherosclerosis as well as in preventing heart attacks and strokes.

SUMMARY OF THE INVENTION

This invention relates to a process for preparing a compound of the formula

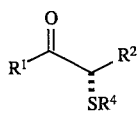
(III)

or

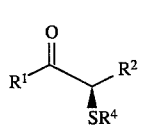
(III')

wherein $R^1$ is selected from the group consisting of hydroxy, $(C_1-C_6)$ alkoxy, benzyloxy wherein the benzyl moiety may optionally be substituted with from one to three substituents independently selected from the group consisting of $(C_1-C_6)$alkyl, $(C_1-C_6)$ alkoxy, $(C_1-C_6)$alkylthio, halo (e.g., chloro, fluoro, bromo or iodo), nitro and trifluoromethyl, or $R^1$ is $NHR^5$ wherein $R^5$ is

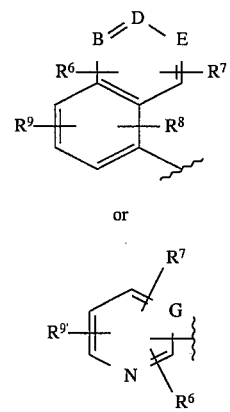

wherein B, D, E and G are independently carbon or nitrogen, with the proviso that at least one of B, D and E is nitrogen, and $R^6$, $R^7$, $R^8$ and $R^9$ are each independently selected from the group consisting of hydrogen, $(C_1-C_6)$alkyl, $(C_1-C_6)$alkoxy, $(C_1-C_6)$alkylthio, $(C_5-C_7)$cycloalkylthio and $NR^{10}R^{11}$, wherein $R^{10}$ and $R^{11}$ are independently selected from hydrogen and $(C_1-C_6)$alkyl, and wherein $R^6$, $R^7$, $R^8$ and $R^9$, when attached to a bicyclic system of formula A, may be attached to either ring of such system, with the proviso that no more than 3 non-hydrogen substituents may be attached to any one ring of such system; $R^2$ is a hydrocarbon containing 6 to 12 carbons; $R^4$ is selected from the group consisting of $(C_4-C_{12})$ straight or branched alkyl, $(C_4-C_{12})$ cycloalkyl-$(C_1-C_6)$alkyl, phenyl, substituted phenyl, $(C_1-C_6)$alkyl-phenyl or $(C_1-C_6)$alkyl-(substituted phenyl), wherein there may be from 1 to 3 substituents on the substituted phenyl moieties and wherein such substituents are independently selected from the group consisting of $(C_1-C_6)$alkoxy, $(C_1-C_6)$alkylthio, $(C_1-C_6)$alkyl, halo (e.g. fluoro, chloro, bromo or iodo) and trifluoromethyl;

comprising reacting, respectively, a compound of the formula

(II)

or

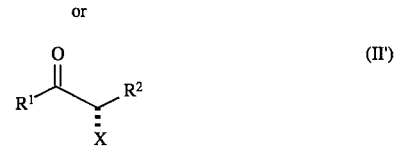
(II')

wherein $R^1$ and $R^2$ are defined as above and X is a leaving group (e.g., chloro, fluoro, bromo, iodo and

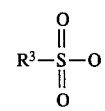

wherein $R^3$ is selected from $(C_1-C_7)$alkyl, trifluoromethyl, and phenyl optionally substituted with $(C_1-C_7)$alkyl, chloro, fluoro, bromo, iodo or nitro), with a compound of the formula $HSR^4$, wherein $R^4$ is defined as above, in the presence of a base, or with a metal salt of the formula $MSR^4$ wherein M is an alkali or alkaline earth metal and $R^4$ is defined as above.

Compounds of the formulae III, III' wherein $R^1=NHR^5$ and mixtures thereof are ACAT inhibitors.

This invention also relates to a process for preparing a compound of the formula III or III', as defined above, comprising: (a) reacting a compound of the formula

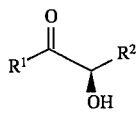 (I)

or

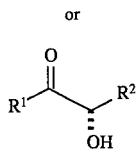 (I')

wherein $R^1$ and $R^2$ are defined as above, respectively with a compound of the formula

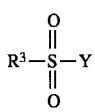

wherein Y is chloro, fluoro, bromo, iodo or $OSO_2R^3$ wherein $R^3$ is defined as above, in the presence of a base, to form, respectively, a compound of the formula II or II', as defined above and wherein X is $OSO_2R^3$; and (b) reacting the compound of formula II or II' so formed with a compound of the formula $HSR^4$, wherein $R^4$ is defined as above, in the presence of a base, or with a metal salt of the formula $MSR^4$ wherein M is an alkali or alkaline earth metal and $R^4$ is defined as above.

This invention also relates to a method of preparing compounds of the formula

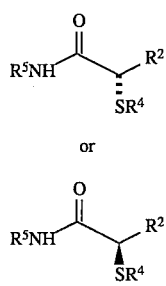 (V)

or

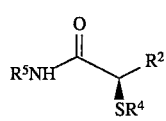 (V')

wherein $R^4$ and $R^5$ are defined as above, comprising reacting a compound of the formula $HSR^4$, wherein $R^4$ is defined as above, or with a metal salt of the formula $MSR^4$ wherein M is an alkali or alkaline earth metal and $R^4$ is defined as above, with, respectively, a compound of the formula

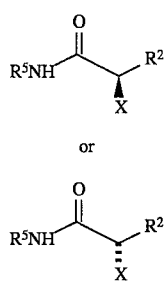 (XV)

or

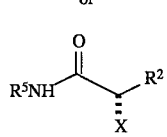 (XV')

wherein $R^2$, $R^5$ and X are defined as above, in the presence of a base.

This invention also relates to a process of preparing a compound of the formula

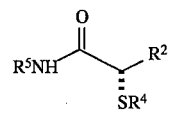 (V)

or

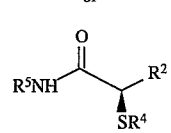 (V')

wherein $R^2$, $R^4$ and $R^5$ are defined as above comprising:
(a) reacting, respectively, a compound of the formula

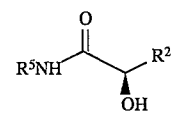 (XVI)

or

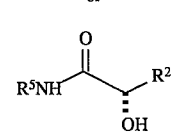 (XVI')

wherein $R^2$ and $R^5$ are defined as above in the presence of a base, to form, respectively, a compound of the formula

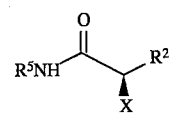 (XVII)

or

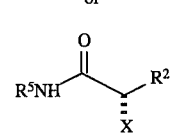 (XVII')

wherein $R^2$ and $R^5$ are defined as above and X is $OSO_2R^3$, and $R^3$ is defined as above, and
(b) reacting the compound of formula XVII or XVII' so formed with a compound of the formula $HSR^4$, wherein $R^4$ is defined as above, in the presence of a base, or with a metal salt of the formula $MSR^4$ wherein M is an alkali or alkaline earth metal and $R^4$ is defined as above.

This invention also relates to a method of preparing compounds of the formula

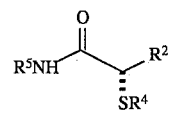 (V)

or

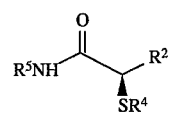 (V')

wherein $R^4$ and $R^5$ are defined as above, comprising reacting a compound of the formula $HNHR^5$ with, respectively, a compound of the formula

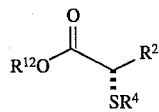 (XIV)

or

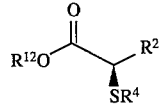 (XIV')

wherein $R^2$ and $R^4$ are defined as above and $R^{12}$ is $(C_1-C_6)$alkoxy or benzyloxy, in the presence of a Lewis acid.

This invention also relates to a process for preparing a compound of the formula

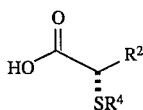 (IV)

or

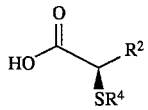 (IV')

wherein $R^2$ and $R^4$ are defined as above, comprising reacting, respectively, a compound of the formula

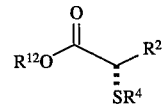 (XIV)

or

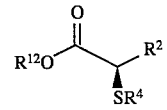 (XIV')

wherein $R^2$, $R^4$ and $R^{12}$ are defined as above, with iodotrimethyl silane.

This invention also relates to a process for preparing a compound of the formula

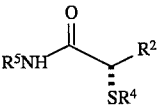 (V)

or

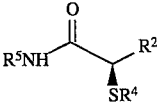 (V')

wherein $R^2$, $R^4$ and $R^5$ are defined as above, comprising:
(a) reacting, respectively, a compound of the formula

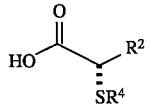 (IV)

or

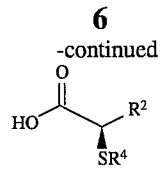 (IV')

wherein $R^2$ and $R^4$ are defined as above with an acid halide an anhydride or a coupling agent to form an active acylating compound; and (b) reacting the active acylating compound so formed with a compound of the formula $NH_2R^5$ wherein $R^5$ is defined as above. In a preferred embodiment of this invention, the acid halide is selected from thionyl chloride, oxalylchloride, phosphorous trichloride, phosphorous pentachloride, phosphorous tribromide, phosphorous pentabromide and phosphorous oxychloride. In a preferred embodiment of this invention the coupling agent is selected from dicyclohexylcarbodiimide, N,N' carbonyldiimidazole, and N-ethoxy-carbonyl-2-ethoxy-1,2 dihydroquinoline.

This invention also relates to a process of preparing compounds of the formula

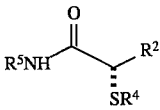 (V)

or

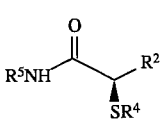 (V')

wherein $R^4$ is selected from the group consisting of $(C_4-C_{12})$ straight or branched alkyl, $(C_4-C_{12})$cycloalkyl-$(C_1-C_6)$alkyl, phenyl, substituted phenyl, $(C_1-C_6)$alkyl-phenyl or $(C_1-C_6)$alkyl-(substituted phenyl), wherein there may be from 1 to 3 substituents on the substituted phenyl moieties and wherein such substituents are independently selected from the group consisting of $(C_1-C_6)$alkoxy, $(C_1-C_6)$alkylthio, $(C_1-C_6)$alkyl, halo (e.g. fluoro, chloro, bromo or iodo) and trifluoromethyl; $R^5$ is

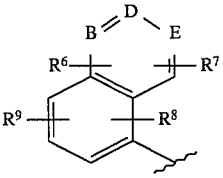

or

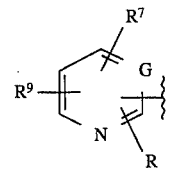

wherein B, D, E and G are independently carbon or nitrogen with the proviso that at least one of B, D and E is nitrogen, $R^6$, $R^7$, $R^8$ and $R^9$ are each independently selected from the group consisting of hydrogen, $(C_1-C_6)$alkyl, $(C_1-C_6)$alkoxy, $(C_1-C_6)$alkylthio, $(C_5-C_7)$cycloalkythio and $NR^{10}R^{11}$, wherein $R^{10}$ and $R^{11}$ are independently selected from the group consisting of hydrogen and $(C_1-C_6)$alkyl, and wherein $R^6$, $R^7$, $R^8$ and $R^9$, when attached to a bicyclic system of formula A, may be attached to either ring of such system, with the proviso that no more than 3 non-hydrogen substituents may be attached to any one ring of such system; and $R^2$ is a hydrocarbon containing 6 to 12 carbon atoms;

comprising reacting, respectively, a compound of the formula

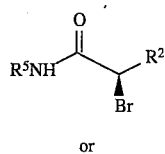

(XVa)

or

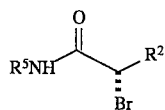

(XVa')

wherein $R^5$ and $R^2$ are defined as above, with either a compound of the formula $HSR^4$, wherein $R^4$ is defined as above, in the presence of a base, or with a compound of the formula $MSR^4$ wherein M is an alkali or alkaline earth metal and $R^4$ is defined as above.

This invention also relates to a method of preparing (S)-methyl-2-hexylthiodecanoate or (R)-methyl-2-hexylthiodecanoate, comprising: (a) reacting (R)-methyl-2-hydroxydecanoate or (S)-methyl-2-hydroxydecanoate, respectively, with trifluoromethanesulfonic anhydride (triflic anhydride) in the presence of a base to form (R)-methyl-2-trifluoromethanesulfonatedecanoate or (S)-methyl-2-trifluoromethanesulfonatedecanoate, respectively; and (b) reacting the (R)-methyl-2-trifluoromethanesulfonate-decanoate or (S)-methyl-2-trifluoromethanesulfonate-decanoate so formed with hexanethiol in the presence of a base.

This invention also relates to a method of preparing (S)-methyl-2-hexylthiodecanoate or (R)-methyl-2-hexylthiodecanoate, comprising: (a) reacting (S)-methyl-2-hydroxydecanoate or (R)-methyl-2-hydroxydecanoate, respectively, with methanesulfonic acid, diisopropyl azodicarboxylate, triphenylphosphine, and a base to form (R)-methyl-2-methanesulfonatedecanoate or (S)-methyl-2-methanesulfonatedecanoate, respectively; and (b) reacting the (R)-methyl-2-methanesulfonate-decanoate or (S)-methyl-2-methanesulfonate-decanoate so formed with hexanethiol in the presence of a base.

This invention also relates to a method of preparing (R)-methyl-2-hydroxydecanoate and (S)-2-hydroxydecanoic acid, comprising reacting racemic methyl-2-hydroxydecanoate with Lipase P-30.

This invention also relates to a method of preparing either (R)-methylbenzylammonium-(2R)-hydroxydecanoate and (R)-methylbenzylammonium-(2S)-hydroxydecanoate, or (S)-methylbenzylammonium-(2R)-hydroxydecanoate and (S)-methylbenzylammonium-(2S)-hydroxydecanoate, comprising reacting, respectively, (R)-(+)-α-methylbenzylamine or (S)-(−)-α-methylbenzylamine with 2-hydroxydecanoic acid.

This invention also relates to a method of preparing (S)-(−)-2-bromodecanoic acid or (R)-(+)-2-bromodecanoic acid, comprising reacting, respectively, (S)-2-aminodecanoic acid or (R)-2-aminodecanoic acid with sodium or potassium nitrite and an alkali or alkaline earth metal bromide in the presence of an acid.

This invention also relates to the following diastereomeric salts: (R)-methylbenzylammonium-(2R)-hydroxydecanoate, (R)-methylbenzylammonium-(2S)-hydroxydecanoate, (S)-methylbenzylammonium-(2R)-hydroxydecanoate and (S)-methylbenzylammonium-(2S)-hydroxydecanoate.

This invention also relates to dicyclohexylammonium-(S)-hexylthiodecanoate, and dicyclohexylammonium-(R)-hexylthiodecanoate and important salt used to purify the intermediates (S)-hexylthiodecanoic acid and (R)-hexylthiodecanoic acid.

This invention also relates to compounds of the formula

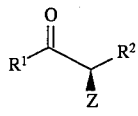

(II-A)

or

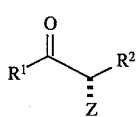

(II-A')

wherein Z is OH or X and $R^1$, $R^2$ and X are defined as above.

This invention also relates to compounds of the formula

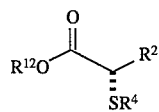

(XIV)

or

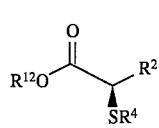

(XIV')

wherein $R^2$, $R^4$ and $R^{12}$ are defined as above.

DETAILED DESCRIPTION OF THE INVENTION

The following reaction schemes and discussion illustrate the processes of the present invention. They also illustrate methods of preparing the compounds of the invention.

In the reaction schemes and discussion that follow, unless otherwise indicated, $R^1$ through $R^{12}$, X, Y and Z and structural formulas I, I', II, II', IIIa, IIIa', V, V', XV, XV', XVI and XVI' are defined as above.

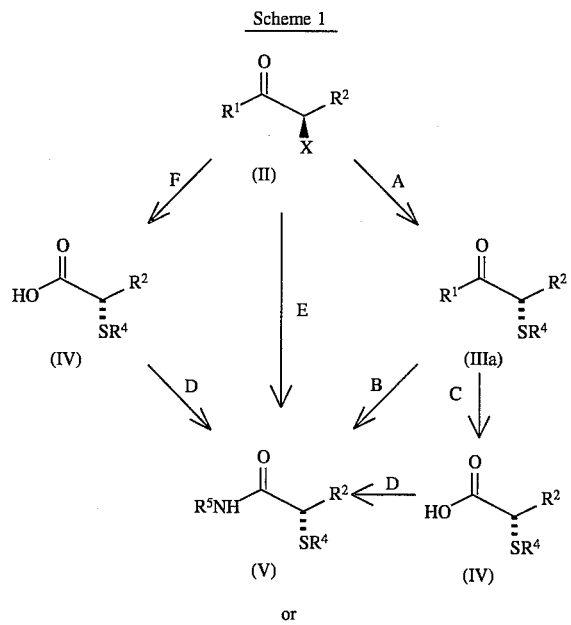

Scheme 1

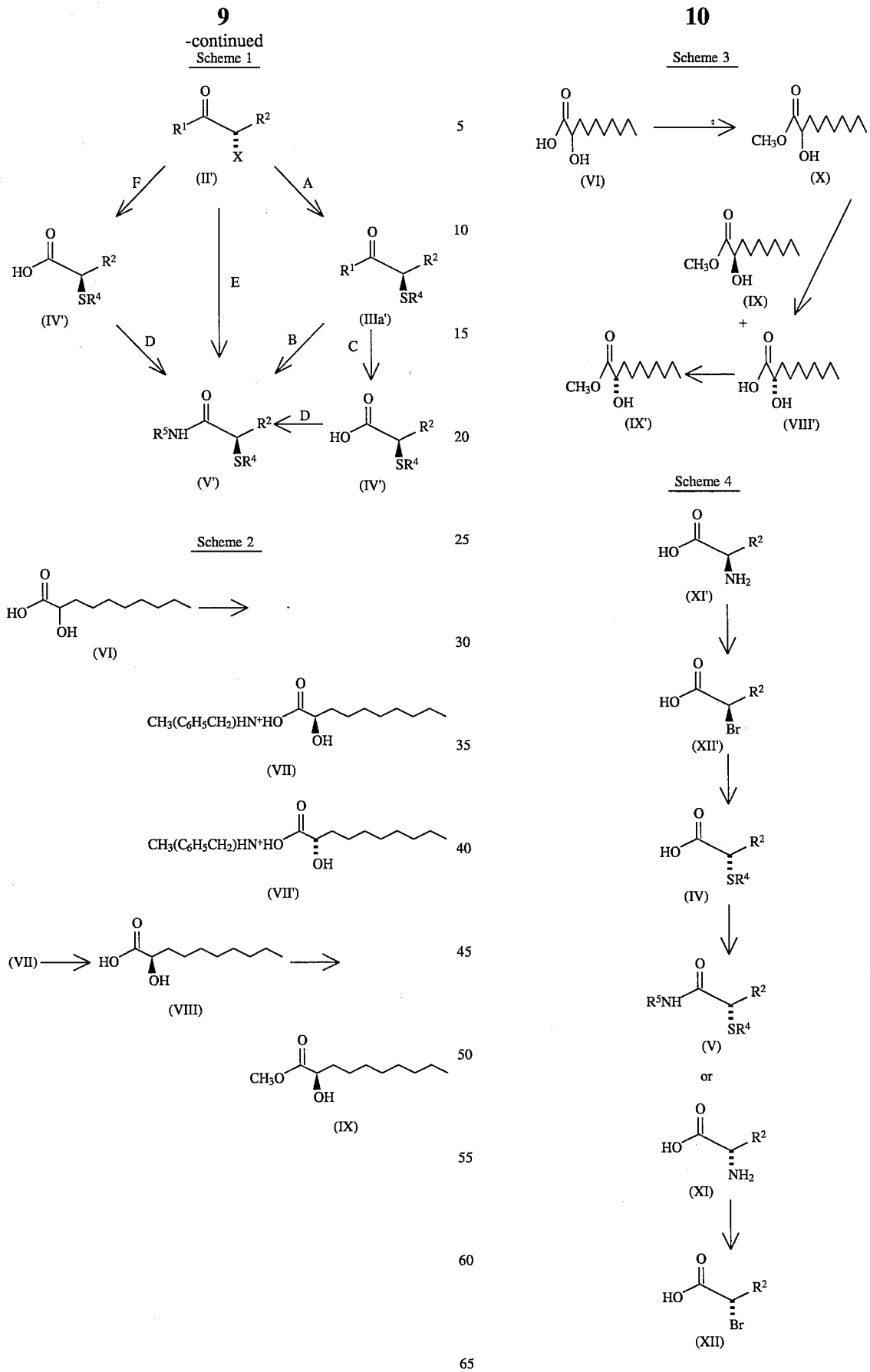

-continued
Scheme 4

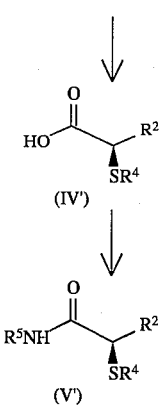

Scheme 5

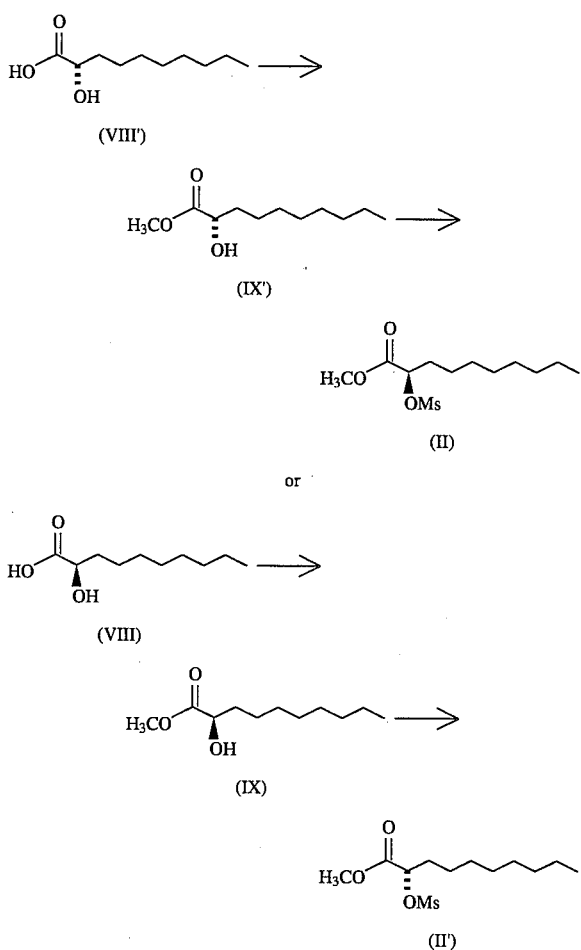

Referring to scheme 1, reaction A (i.e., II→IIIa) illustrates the thiol displacement reaction that converts compounds of the formula II or II' wherein $R^1$ is other than hydroxy or $NHR^5$ to, respectively, the corresponding compounds of the formula IIIa or IIIa'. This reaction results in inversion of the stereochemistry at the carbon atom alpha to the carbonyl group and may be used to produce the desired thiol substituted product of either stereochemistry (i.e., a compound of the formula IIIa or IIIa') depending on the nature of the starting material (i.e., a compound of the formula II or II', respectively).

The thiol displacement is carried out by reacting a compound of the formula II or II' with the appropriate compound of the formula $HSR^4$ in the presence of a base, or with a metal salt of the formula $MSR^4$ wherein M is an alkali or alkaline earth metal and $R^4$ is defined as above. Suitable bases include tertiary amines (e.g., triethylamine or pyridine), metal carbonates (e.g., cesium or potassium carbonate), metal hydrides (e.g., sodium or potassium hydride), metal hydroxides (e.g., sodium or potassium hydroxide), substituted guanidines (e.g., tetramethylguanidine) and metal alkoxides (e.g., potassium tert-butoxide or sodium methoxide). Generally, the solvent is an inert, polar solvent. Examples of appropriate solvents are methylene chloride ($CH_2Cl_2$), acetonitrile ($CH_3CN$), tetrahydrofuran (THF) and toluene. Reaction temperatures may range from about 31 78° C. to about 100° C. Preferably, the thiol displacement is carried out in the presence of triethylamine (TEA) in acetonitrile at a temperature from about −30° C. to about 35° C.

Where $R^1$ is methoxy, compounds of the formula IIIa or IIIa', obtained as described above, may be converted, respectively, to the corresponding compounds of the formula

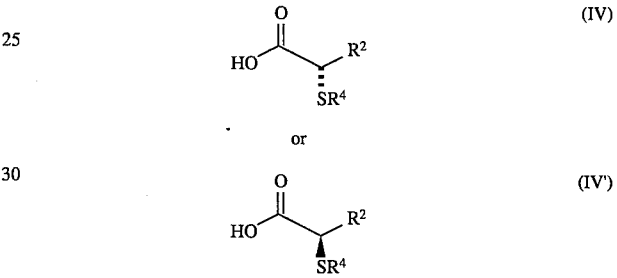

respectively, by reacting them with trimethylsilyl iodide (which may be generated by a variety of methods known in the art, e.g. using trimethylsilyl chloride and sodium iodide or commercial trimethylsilyl iodide) in a polar, aprotic solvent such as acetonitrile, $CH_2Cl_2$, dimethylsulfoxide (DMSO) or dimethylformamide (DMF), at a temperature from about 15° C. to about the reflux temperature of the solvent. This procedure is illustrated in reaction C of scheme 1. Preferably, the reaction is cried out either in acetonitrile with trimethylsilyl chloride and sodium iodide at about 55° C. in the presence of an iodine catalyst, or in hexamethyldisilane and iodine, either neat or in one of the foregoing protic apolar solvents. Compounds of the formula IIIa or IIIa' wherein $R^1$ is other than methoxy, hydroxy or $NHR^5$, obtained as described above, may be converted to the corresponding acids of formula IV and IV', respectively, by methods known in the art.

As shown in step D of scheme 1, reaction of the products of formula IV or IV' with an amine of the formula $R^5NH_2$ yields the corresponding ACAT inhibitors of formula V or V', respectively. This reaction is carried out by formation of an activated acid such as an acid chloride or anhydride. The amide formation reaction is typically conducted in a polar, aprotic solvent such as pyridine/methylene chloride, in the presence of oxalyl chloride and a catalytic amount of DMF, at a temperature from about 0° C. to about 50° C.

Both the formation of acids of the formula IV and IV' and the formation of amides of the formula V and V' occur with preservation of the stereochemistry at the carbon alpha to the carbonyl group and may be used to form products of either stereochemistry by choosing the appropriate starting material.

Reaction B of scheme 1 illustrates a method of preparing ACAT inhibitors of the formula V' from the corresponding esters of the formula IIIa wherein $R^1$ is other than hydroxy or $R^5NH$. The esters are reacted with the appropriate compound of the formula $NHR^5$ in the presence of a Lewis acid. Suitable Lewis acids include tin (II) chloride, titanium (IV) chloride, titanium IV propoxide, trimethylaluminum, zinc chloride and ethylaluminum dichloride. Trimethylaluminum is preferred. Typically, the solvent is an inert, polar solvent such as methylene chloride, ether or toluene; with methylene chloride being preferred. Reaction temperatures may range from about 20° C. to about 100° C., with about 55° C. being preferred. This reaction preserves the stereochemistry at the carbon alpha to the carbonyl group, and may be used to produce ACAT inhibitors of the formula V or V', by choosing a starting material having the desired stereochemistry.

Compounds of the formula II and II' wherein $R^1$ is $NHR^5$ may be converted directly to the corresponding ACAT inhibitors of formula V or V', as illustrated in reaction E of scheme 1, by the thiol displacement described above for reaction A of scheme 1.

Compounds of the formula II or II' wherein $R^1$ is hydroxy and X is chloro, fluoro, bromo, or iodo may be converted to the corresponding ACAT inhibitors of formula V or V' by the reaction sequence shown in steps F and D of scheme 1. According to this procedure, a compound of the formula II or II' is subjected to the thiol displacement described above for step A to form, respectively, a thiol acid of the formula IV or IV' (step F). The thiol acid is then reacted with the appropriate amine of the formula $NHR^5$, as described above for step D, to form the corresponding amide.

Compounds of the formula II or II' wherein X is $OSO_2R^3$ may be prepared by reacting, respectively, a compound of formula I or I' with the appropriate compound of the formula

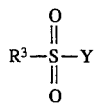

in the presence of a base. Suitable and preferred bases, solvents and conditions for this reaction are the same as those described above for the thiol displacement step. The products of formula II or II' may be generated in situ or isolated for use in the thiol displacement step.

This reaction, unlike the thiol displacement, preserves the stereochemistry at the carbon alpha to the carbonyl group. It can be used to prepare X-substituted products of either stereochemistry (i.e., compounds of the formula II or II') by choosing the appropriate starting material having the same stereochemistry (i.e., a compound of formula I or I', respectively).

Compounds of the formula II or II', wherein $R^1$ is hydroxy and X is chloro, fluoro, bromo or iodo may be prepared from their 2-amino carboxylic acid counterparts, as illustrated in scheme 4 for the preparation of the bromo acid of formula XII or XII' from the amino acid of formula XI or XI', respectively. The 2-amino carboxylic acids are converted to their 2-halo counterparts having the same stereochemistry at the carbon alpha to the carbonyl group by reacting them with sodium or potassium nitrite and an alkali or alkaline earth metal halide in the presence of an acid. Examples of suitable acids that may be used are sulfuric acid and hydrochloric acids. This reaction is generally conducted in an aqueous solvent at a temperature from about −30° C. to about 100° C., with about 0° C. being preferred.

As indicated above, schemes 2 and 3 illustrate how certain starting materials for the reaction sequence of scheme 1 may be prepared by resolving 2-hydroxydecanoic acid using the novel processes of this invention.

Referring to scheme 2, racemic 2-hydroxydecanoic acid is converted into the diasteriomeric salts (R)-methylbenzylammonium-(2R)-hydroxydecanoate (VII) and (R)-methylbenzylammonium-(2S)-hydroxydecanoate (VII') by reacting it with (R)-(+)-α-methylbenzylamine. Alternatively, racemic 2-hydroxydecanoic acid may be reacted with (S)-(−)-α-methylbenzylamine to produce the diasteriomeric salts (S)-methylbenzylammonium-(2R)-hydroxydecanoate and (S)-methylbenzylammonium-(2S)-hydroxydecanoate. These reactions are typically conducted at a temperature from about −78° C. to about 100° C., preferably from about 20° C. to about 50° C., in a nonpolar aprotic solvent that may optionally be combined with a polar solvent. Examples of suitable solvents include hexane, toluene, water, acetone and mixtures of two or more of these solvents. A mixture of acetone and hexane is preferred.

Either of the diastereomeric salts so formed may then be reacted with a mineral or organic acid (e.g., sulfuric or acetic acid) in an inert solvent such as ethylacetate, water, acetone or toluene, preferably ethyl acetate, to yield the pure enantiomer of 2-hydroxydecanoic acid having the same stereochemistry at the carbon alpha to the carbonyl group (e.g., VII→VIII in scheme 2). The reaction temperature may range from about −78° C. to about 100° C., but is preferably about room temperature. Either of the resulting pure enantiomers of 2-hydroxydecanoic acid can then be converted into the pure enantiomer of methyl-2-hydroxydecanoate having the same stereochemistry at the carbon alpha to the carbonyl group by treatment with methanol and hydrochloric acid at a temperature from about −78° C. to about 100° C. (e.g., VIII→IX in scheme 2). The solvent may be methanol or another inert, polar, aprotic solvent such as methanol/THF, methanol/methylene chloride or methanol/toluene.

The enantiomerically pure methyl esters obtained as described above may be used as starting materials for the preparation of ACAT inhibitors of the formula V and V' according to the procedure of scheme 1 (i.e., II→IIIa→IV →V or II→IIIa→V).

An alternate novel method of resolving 2-hydroxydecanoic acid is illustrated in scheme 3. According to this method, racemic 2-hydroxydecanoic acid (VI) is first converted to the racemic methyl ester (X) by reacting it with methanol and hydrochloric acid as described for the analogous reaction in scheme 2 (VIII→IX). The racemic methyl ester (X) is then reacted with Lipase P-30 to form (R)-methyl-2-hydroxydecanoate (IX) and (S)-2-hydroxydecanoic acid (VIII'). This reaction is typically carried out at a temperature from about 5° C. to about 55° C. in water or a water miscible solvent, or at the organic/aqueous interface of a water miscible solvent and an organic cosolvent. Examples of appropriate solvents are dimethylsulfoxide (DMSO)/water, toluene/water, methanol/water, hexane/water and tetrahydrofuran (THF)/water. The preferred temperature is from about 20° C. to about 50° C. and the preferred solvent is water. The pH is generally maintained at about 6.0 to about 8.0.

The enantiomerically pure methyl ester of formula IX ((R)-methyl-2-hydroxydecanoate) may be used to prepare ACAT inhibitors of the formula V by subjecting it to the reaction sequence of scheme 1 (i.e., II→IIIa→IV→V or II→IIIa →V). Because the thiol displacement reaction of scheme 1 (i.e., II→IIIa) inverts the stereochemistry at the carbon alpha to the carbonyl groups, the combination of these procedures yields exclusively ACAT inhibitors of the formula V.

ACAT inhibitors of the formula V' may be prepared by converting the enantiomerically pure (2S)-2-hydroxydecanoic acid obtained from the Lipase P-30 resolution to the methyl ester, of the formula IX', having the same stereochemistry at the alpha carbon, and then subjecting the methyl ester so formed to the reaction sequence of scheme 1.

Alternatively, IX'or IX may be recycled by Mitsunobu inversion of the hydroxy carbon steriochemistry by forming a mesylate group, as illustrated in Scheme 5. Compounds of the formula II or II' wherein X is $OSO_2CH_3$ may be prepared by reacting respectively the compound of the formula IX' or IX with methanesulfonic acid, a base, triphenylphosphine and dialkyl ($C_1$–$C_6$)azodicarboxylate preferably diisopropyl azodicarboxylate. Reaction temperatures may range from about 20° C. to about 100° C., with 75° C. being preferred. Suitable bases can be chosen from any of the available hindered amine bases, triethylamine being preferred. Generally, the solvent is inert, such as methylene chloride, ether, or toluene, with toluene being preferred. This reaction, like the thiol displacement, inverts the stereochemistry at the carbon alpha to the carbonyl group. It can be used to prepare X substituted products of either stereochemistry (i.e., compounds of the formula II or II') by choosing the appropriate starting material having the opposite stereochemistry (i.e., a compound of formula IX' or IX, respectively).

For each of the processes described above, except where otherwise indicated, pressure is not critical. Pressures from about 0.5 atmospheres to about 5.0 atmospheres are generally suitable, and ambient pressure, (i.e., about 1 atmosphere) is preferred as a matter of convenience.

The following examples illustrate but do not limit the scope of the present invention.

Melting points were determined with a Thomas-Hoover capillary melting point apparatus and were uncorrected. NMR spectra were recorded on a Bruker 300-MHz spectrometer in $CDCl_3$, unless otherwise noted. Infrared spectra were recorded on a Perkin-Elmer 283B spectrophotometer and were performed on neat samples. Flash chromatography was performed using Kieselgel 60 (trademark) (230–400 mesh). All reagents were used as received without further purification.

EXAMPLE 1

(R)-(+)-α-Methylbenzylammonium-2-hydroxydecanoate

Racemic 2-hydroxydecanoic acid (M. N. Camien and M. S. Dunn, J. Biol. Chem. 211, 593 (1954)) (74 g, 0.393 mol) was suspended in 1.8 L of 5% acetone in hexane. R-(+)-α-Methylbenzylamine (50.7 mL, 47.6 g, 0.393 mol) was added and the reaction was stirred at room temperature for 1.5 hours. R-(+)-α-Methylbenzylammonium (2R)-2-hydroxydecanoate (60.0 g, 0.194 mol, 49%) was collected by filtration. The salt was further purified by recrystallization from a 10% solution of acetone in hexane (600 mL) to give R-(+)-α-Methylbenzylammonium (2R)-2-hydroxydecanoate (43.43 g, 0.14 mol, 36%) as a white solid: mp 94°–95° C.; $[\alpha]_D$=+17.7°(c=1, MeOH). Anal. Calcd. for $C_{18}H_{29}NO_3$: C, 69.87; H, 9.45; N, 4.53: Found: C, 69.83; H, 9.86; N, 4.50%.

EXAMPLE 2

(R)-2-Hydroxydecanoic Acid

R-(+)-α-Methylbenzylammonium (2R-2-hydroxydecanoate (42.43 g, 0.137 mol) was placed in 140 mL of ethyl acetate. 140 mL of 1N HCl was added and the mixture stirred for 0.5 hours. The organic phase was separated, washed with 30 mL portions of 1N HCl and brine and dried ($MgSO_4$). Following concentration (R)-2-hydroxydecanoic acid (25.63 g, 0.136 mol, 99%) was isolated as a white solid: mp 77.5°–78.5° C.; $[\alpha]_D$=–4.9° (c=1, $CHCl_3$); IR($CHCl_3$) 3657, 3517, 3385, 1602, 1457, 1343, 1261, 1210, 1127, 1088, 1034, 893, 751 cm-1; $^1$H NMR δ4.25 (dd, 1 H, J=4.2, 7.5 Hz), 1.83–1.25 (m, 14H), 0.85 (t, 3H, J=5.4 Hz); $^{13}$C NMR δ179.57, 70.36, 34.04, 31.84, 29.39, 29.27, 29.23, 24.78, 22.65, 14.04. Anal. Calcd. for $C_{10}H_{20}O_3$:C, 63.80; H, 10.71: Found: C, 63.84: H, 10.84%.

EXAMPLE 3

(R)-Methyl -2-Hydroxydecanoate

Acetyl chloride (21 mL, 0.295 mol) was added to 225 ml of methanol at 0° C. The acidic methanol solution was added to (R)-2-Hydroxydecanoic acid (15.96 g, 0.0847 mol) in 200 mL of methanol at 0° C. The reaction was allowed to warm to room temperature and stirred for 12 hours. The reaction was quenched by addition of a saturated solution of $NaHCO_3$ and the pH adjusted to 9. The aqueous methanol was extracted with two 800 mL portions of hexane. The combined hexane extracts were dried ($MgSO_4$) and concentrated to (R)-methyl-2-hydroxydecanoate (17.10 g, 0.0845 mol, 99%) as clear oil: $[\alpha]_D$=–3.9° (c=1.2, MeOH); IR($CHCl_3$) 3665, 3535, 2853, 1601, 1439, 1377, 1262, 1220, 1130, 1089, 1000, 634 cm$^{-1}$; $^1$H NMR δ 4.16 (m, 1H), 3.75 (s, 3H), 2.80 (m, 1H), 1.77–1.24 (m, 14H), 0.85 (t, 3H, J=6.50 Hz). Anal. Calcd. for $C_{11}H_{22}O_3$: C, 65.30; H, 10.96: Found: C, 65.00; H, 11.33%.

EXAMPLE 4

(S)-2-Hydroxydecanoic Acid

Lipase P-30 (Amano from Pseudomonas fluorescens) (1 g, 5% by weight) was dissolved in 140 ml of $H_2O$ and the pH of the solution adjusted to 7.5 with a 1N solution of NaOH. Racemic methyl 2-hydroxydecanoate (20.12 g, 0.995 mol) (CP-112,994) was added to the enzyme solution and the pH controlled to maintain a range of 6–8. The reaction was stirred at room temperature for 10 hours (total of 46.5 mL of 1N NaOH added) and worked up by addition of 140 ml of methanol. The aqueous alcohol was extracted with hexane (3×200 mL). The hexane extracts were combined and dried ($MgSO_4$). Following concentration, the desired (R)-methyl-2-hyroxydecanoate (10.08 g, 0.049 mol, 50%) was obtained: $[\alpha]_D$=–3.1° (c=1, MeOH). The aqueous extracts were acidified to pH 1–2 with HCl and extracted with two portions of ethyl acetate (200 mL). The combined extracts were dried ($MgSO_4$) and concentrated to give (S)-2-hydroxydecanoic acid (8.91 g, 0.047 mol, 47%): mp 70°–72°; $[\alpha]_D$=–1.7° (c=1, MeOH).

Enriched (R)-methyl-2-hydroxydecanoate (9.95 g, 0.049 mol) from the initial hydrolysis was resubjected to the identical reaction conditions using Lipase P-30 (1.02 g, 10% by weight) in $H_2O$ (40 mL). The pH was controlled by the addition of 1N NaOH. After 4 hours, 5.4 mL of base had been added and the reaction was stopped by the of $H_2O$ (50 mL) and MeOH (30 mL) and extracted with hexane (3×200 mL), the combined organic layers were filtered, washed in brine and dried ($MgSO_4$). Following concentration, the desired (R)-methyl-2-hydroxydecanoate (8.64 g, 0.043 mol, 87%) (CP-114,253) was obtained: $[\alpha]_D$=–3.8° (C=1, MeOH).

Alternatively, the racemic hydroxyester (16.2 g, 8013 mmol) can be dissolved in toluene (65 mL) and $H_2O$ (150 mL) added. The pH was adjusted by the addition of 1N NaOH and the enzyme (0.81 g, 5% by weight) added to the solution. After 33 hours the reaction had consumed 37.4 mL of 1N NaOH. The reaction was quenched by addition of Darco (4.6 g), hexane (150 mL) and Celite (10.4 g) and stirred for 0.25 hours. The reaction mixture was filtered over a bed of Celite (12 g) and the filter washed with hexane (3×200 mL). Each of the hexane washes was used to extract the aqueous phase. The combined organic layer was washed with $H_2O$ and brine, dried and concentrated to give (R)-methyl-2-hydroxydecanoate (6.20 g, 0.031 mol, 38%): [α]$_D$=−3.2° c=1, MeOH).

Alternatively, the racemic hydroxyester (5.35 g, 26.5 mmol) can be dissolved in MeOH (24 mL) and $H_2O$ (56 mL) added. The enzyme was added (0.268 g, 5% by weight) and the pH adjusted by the addition of 1N NaOH. The reaction was stirred at ambient temperature for 55 hours by which time 15.0 mL of base had been added. Hexane (150 mL) was added in addition to Celite (2 g) and the reaction stirred for 0.25 hours. The reaction was filtered through Celite (6 g) and the filter washed with hexane (50 mL). The filter was washed with hexane (2×150 mL) and each of the hexane washes used to extract the aqueous methanol layer. The combined organic phase was washed with brine and dried ($MgSO_4$) to obtain (R)-methyl 2-hydroxydecanoate (2.27 g, 0.011 mol, 43%): [α]$_D$=−3.5° (c=1, MeOH).

EXAMPLE 5

(S)-Methyl-2-hexylthiodecanoate (R)-Methyl-2-hydroxydecanoate (202.3 g, 1.00 mol) was dissolved of in 5 L of dry acetonitrile. The vessel was flushed with nitrogen and cooled to an internal temperature of −25° C. Triflic anhydride (185 mL, 310 g, 1.10 mol) was added slowly followed by triethylamine (TEA) (150 mL, 111 g, 1.10 mol) at such a rate that the internal temperature stayed below −20° C.

Hexanethiol (193 mL, 162 g, 1.30 mol) was added rapidly followed by slow addition of TEA (181 mL, 131 g, 1.30 mol). The reaction was warmed to room temperature and stirred for one hour. TLC (eluting with 10:1 hexanes to ethyl acetate) revealed (S)-methyl-2-hexylthiodecanoate at $R_f$~0.5. The acetonitrile was azeotroped with ethyl acetate. The ethyl acetate was washed with 3 L of water and then with 1 L of brine. The organic layer was dried with $MgSO_4$ and concentrated to an oil. The oil was filtered through silica gel (15 g silica/ g crude product), eluted with hexane and flushed with 30:1 hexane/ethyl acetate to give (S)-methyl-2-hexylthiodecanoate (295 g, 0.97 mol, 97%) as a colorless oil: [α]$_D$=−72.5° (c=1, MeOH); $^1$H NMR δ3.71 (s, 3H), 3.21 (dd, 1H, J=7, 8 Hz), 2.55 (m, 2H), 1.88–1.15 (m, 22H), 0.95 (m, 6H); $^{13}$C NMR δ173.46, 52.05, 46.64, 31.81, 31.46, 31.37, 31.30, 29.30, 29.17, 28.51, 27.38, 22.63, 22.50, 14.06, 13.99; Anal. Calcd. for $C_{17}H_{34}O_2S$:C, 67.50; H, 11.33: Found: C, 67.60; H, 11.45%.

EXAMPLE 6

(S)-Methyl-2-hexylthiodecanoate

Using the procedure outlined in Example 3, (S)-2-hydroxydecanoic acid (3.65 g, 0.019 mol) was converted to (S)-methyl-2-hydroxydecanoate (3.56 g, 0.017 mol, 93%).

Methanesulfonic acid (0.135 mL, 2.08 mmol) was added to toluene (4 mL) followed by triethylamine (0.29 mL, 2.08 mmol) and the reaction stirred for 5 minutes at room temperature. Triphenylphosphine (0.571 g, 2.18 mmol) was added to the pale yellow solution. (S)-Methyl-2-hydroxydecanoate (0.352 g, 1.74 mmol) was dissolved in toluene (1 mL) and added to the reaction mixture. Diisopropyl azodicarboxylate (97%, 0.4 mL, 2.18 mmol) was added slowly and the reaction was heated in a bath at 75° C. for 15 hours. The reaction was concentrated and then taken up in ethyl acetate (60 mL) and the organic layer washed with saturated bicarbonate solution and brine. The organic layer was dried ($MgSO_4$) and concentrated to obtain (R)-methyl-2-methanesulfonate-decanoate. This material was not purified and was taken directly on to the displacement. (R)-Methyl-2-methanesulfonatedecanoate (1.74 mmol, assumed) was dissolved in acetonitrile (10 mL) and hexanethiol (0.49 mL, 3.47 mmol) added to the solution. Tetramethylguanidine (0.22 mL, 1.74 mmol) was added to the reaction and it was stirred at room temperature for 2 hours. The reaction was poured into ethyl acetate (50 mL) and washed with a saturated solution of bicarbonate followed by brine. The organic layer was dried and concentrated to an oilly residue which was purified by silica gel chromatography using hexane and 5 to 1 hexane to ethyl acetate as the eluents to yield (S)-methyl-2-hexylthiodecanoate (0.33 g, 1.09 mmol, 64% for two steps). [α]$_D$=−67.32° (c=0.71, MeOH).

Alternatively this sequence can be combined in one step. (R)-Methyl-2-hydroxydecanoate (0.209 g, 1.03 mmol) was dissolved in acetonitrile (2 mL). To this solution was added methanesulfonic acid (74 μL, 1.14 mmol) and triethylamine (158 μL, 1.14 mmol) followed by diisopropyl azodicarboxylate (97%, 0.33 mL, 1.65 mmol) and finally, triphenylphosphine (0.433 g, 1.65 mmol). The reaction was heated to a bath temperature of 90° C. for 4 hours and then cooled to room temperature (rt). Hexanethiol (0.31 mL, 2.07 mmol) and tetramethyl guanidine (0.26 mL, 2.07 mmol) were added and the reaction stirred at rt for 1 hour the reaction was extracted with hexane (20 mL) and washed with 0.5N HCl (20 mL), 1N HCl (15 mL), and $H_2O$ (15 mL), dried ($MgSO_4$) and concentrated to an oil. The oil was purified by silica gel chromatography using 30 to 1 hexane to ethyl acetate as the eluent to give (R)-methyl-2-hexylthiodecanoate (0.315 g, 1.03 mmol, 100%). [α]$_D$=+53.9° (c=1.3, MeOH).

EXAMPLE 7

(S)-Methyl-2-phenylthiodecanoate

Following the procedure of Example 5, (R)-methyl 2-hydroxydecanoate (0.99 gm, 4.90 mmol) was converted to the triflate with triflic anhydride (0.95 ml, 5.65 mmol) and 2,6-lutidine (0.66 ml, 5.63 mmol). The triflate was displaced with thiophenol (0.62 ml, 5.88 mmol) in the presence of TEA (1.57 ml, 11.3 mmol). The desired (S)-methyl-2-phenylthiodecanoate (1.48 g) was purified by silica gel chromatography (1.00 gm, 3.39 mmol, 69%). [α]$_D$=−101.2° (c=1, MeOH). $^1$H NMR δ7.41 (m, 2H), 7.25 (m, 3H), 3.63 (dd, 1H, J=6.8,8.3 Hz), 3.62 (s, 3H), 1.86 (m, 1H), 1.74 (m, 1H), 1.43–1.24 (m, 12H), 0.86 (t, 3H, J=6.8 Hz).

EXAMPLE 8

(S)-Methyl-2-phenylthiodecanoate (R)-Methyl-2-hydroxydecanoate (1.15 gm, 5.68 mmol) was dissolved in 12 ml of methylene chloride with catalytic 4-dimethylaminopyridine (DMAP). The reaction was cooled to 0° C. and methanesulfonyl chloride (0.53 ml, 6.82 mmol) was added followed by TEA (1.9 ml, 13.6 mmol) and the reaction stirred for 3 hours. The reaction was diluted with 20 ml of ethyl acetate and washed with water (10 ml) and 1N HCl (10 ml). The organic layer was washed with brine, dried ($MgSO_4$) and concentrated to give (R)-methyl-2-methanesulfonate-decanoate as an orange oil (1.39 gm, 4.95 mmol, 87%). $^1$H NMR δ4.99 (dd, 1H, J=7.0, 7.5 Hz), 3.76 (s, 3H), 3.11 (s, 3H), 1.86 (m, 2H), 1.43–1.23 (m, 12H), 0.84 (t, 3H, J=6.8 Hz).

EXAMPLE 9

(R)-Methyl-2-(4-methylphenylsulfonate)decanoate (R)-Methyl-2-hydroxydecanoate (1.02 gm, 5.03 mmol), was dissolved in 10 ml of methylene chloride with catalytic DMAP. The reaction was cooled to 0° C. and tosyl chloride (1.15 g, 6.04 mmol) followed by TEA (1.68 ml, 12.08 mmol) was added. The reaction was allowed to slowly warm to rt and stirring continued for 19 hours. The reaction was diluted with 20 ml of ethyl acetate and washed with 10 ml of water. The organic layer was washed with 1N HCl (10 ml), brined, dried ($MgSO_4$) and concentrated to the desired tosylate as an orange oil (1.90 g). The tosylate was purified by silica gel chromatography using 5 to 1 hexane to ethyl acetate as the eluent to give (R)-methyl-2-(4-methylphenylsulfonate)-decanoate as a clear oil (1.58 g, 4.43 mmol, 88%). $^1H$ NMR δ7.76 (d, 2H, J=8.4 Hz), 7.31 (d, 2H, J=8.4 Hz), 4.76 (dd, 1H, J=5.8, 7.0 Hz), 3.61 (s, 3H), 2.40 (s, 3H), 1.75 (m, 2H), 1.24–1.05 (m, 12H), 0.83 (t, 3H), J=6.8 Hz).

EXAMPLE 10

(S)-Methyl-2-phenylthiodecanoate (R)-Methyl-2-methanesulfonatedecanoate (0.276 g, 0.984 mmol) was dissolved in 1 ml $CH_3CN$. To this solution was added thiophenol (106 µl, 1.03 mmol) and TEA (144 µl, 1.03 mmol) and the reaction was stirred at rt for 12 hours. The reaction was diluted with 5 ml of hexane and washed with 5 ml of basic MeOH (5.4 gm $NaHCO_3$ and 200 ml of $H_2O$ diluted to 1 L with MeOH), 5 ml of $H_2O$ and then brined, dried ($MgSO_4$) and concentrated to give (S)-methyl-2-phenylthiodecanoate (0.253 g, 0.859 mmol, 87%) as a clear oil $[α]_D=-100.2°$ (c=1, MeOH).

Using the procedure outlined above, (R)-methyl-2-methanesulfonatedecanoate (0.286 g, 1.02 mmol) was treated with thiophenol (110 µl, 1.07 mmol) to produce (S)-methyl-2-phenylthiodecanoate (0.255 g, 0.865 mmol, 85%). $[α]_D=-94.5°$ (c=1, MeOH). Anal. Calcd. for $C_{17}H_{26}O_2S$: C, 69.34; H, 8.90: Found: C, 68.97; H, 8.80%.

EXAMPLE 11

(S)-Methyl-2-hexylthiodecanoate

Using the procedure outlined in Example 10 above, (R)-methyl-2-methanesulfonatedecanoate (0.098 g, 0.35 mmol) was dissolved in $CH_3CN$ (1 mL) and hexanethiol (68 µL, 0.385 mmol) added. To this solution was added tetramethyl guanidine (48 µL, 0.35 mmol) and the reaction stirred at rt for 5 hours. The reaction was extracted with hexane (3×6 mL) and the combined organic phase washed with 1N HCl and dried ($MgSO_4$). Following concentration the desired (S)-methyl-2-hexylthiodecanoate (0.106 g, 0.35 mmol, 100%) was obtained. $[α]_D=-69.0°$ (c=1.05, MeOH). This material could be purified by silica gel chromatography using 30 to 1 hexane to ethyl acetate as the eluent to yield the desired (S)-methyl-2-hexylthiodecanoate (0.098 g, 0.32 mmol, 93%). $[α]_D=71.8°$ (c=1.06, MeOH).

EXAMPLE 12

(S)-Methyl-2-phenylthiodecanoate

Using the procedure of Example 11, (R)-methyl-2-(4-methylphenylsulfonate)decanoate (0.594 g, 1.67 mmol) was treated with thiophenol (0.19 ml, 1.83 mmol) and tetramethyl guanidine (0.23 ml, 1.83 mmol) to produce (S)-methyl-2-phenylthiodecanoate (0.458 g, 1.55 mmol, 93%). $[α]_D=-82.0°$ (c=1.3, MeOH).

EXAMPLE 13

(S)-Methyl-2-hexylthiopropionate (R)-Methyl lactate (0.587 g, 5.55 mmol) was treated as described in Example 5 with triflic anhydride (1.07 ml, 6.38 mmol) and TEA (0.89 ml, 6.39 mmol) in 11 ml of $CH_3CN$. Hexanethiol (1.07 ml, 7.21 mmol) and TEA (1.01 ml, 7.21 mmol) were added and the workup described in Example 5 followed by purification by silica gel chromatography using 25 to 1 hexane to ethyl acetate as eluent gave (S)-methyl-2-hexylthiopropionate as a clear yellow oil (0.737 g, 3.61 mmol, 65%). $[α]_D=-128°$ (c=1, MeOH); $^1N$ NMR δ3.69 (s, 3H), 3.36 (q, 1H, J=7.19 Hz), 2.54 (m, 2H), 1.60–1.17 (m, 8H), 1.39 (d, 3H, J=7.19 Hz), 0.84 (t, 3H, J=6.79 Hz); $^{13}C$ NMR δ173.35, 51.85, 40.70, 31.23, 31.13, 29.11, 28.36, 22.36. 17.00, 13.81.

EXAMPLE 14

(R)-Methyl-2-hexylthioproprionate (S)-Methyl lactate (0.571 g, 5.27 mmol) was carried through the reaction sequence of Example 5 with triflic anhydride (1.02 ml, 6.05 mmol) and 2,6-lutidine (0.71 ml, 6.05 mmol) in 11 ml of $CH_3CN$. Hexanethiol (1.02 ml, 6.84 mmol) and TEA (1.91 ml, 13.7 mmol) were added and the workup described in Example 5 followed by purification by silica gel chromatography using 25 to 1 hexane to ethyl acetate as eluent gave (R)-methyl-2-hexylthiopropionate as a clear yellow oil (0.933 g, 4.56 mmol, 86%). $[α]_D=+130.0°$ (c=1, MeOH). Anal. Calcd. for $C_{10}H_{20}O_2S$: C, 58.78; H, 9.87: Found: D, 58.76; H, 9.99%.

EXAMPLE 15

(S)-Methyl-2-phenylthioproprionate (R)-Methyl lactate (0.553 g, 5.31 mol) was carried through the reaction sequence of Example 5 with triflic anhydride (1.03 ml, 6.11 mmol) and 2,6-lutidine (0.74 ml, 6.38 mmol) in 10 ml of $CH_3CN$. Thiophenol (0.73 ml, 6.91 mmol) and TEA (1.93 ml, 13.8 mmol) were added and the workup described in Example 5 followed by purification by silica gel chromatography using 25 to 1 hexane to ethyl acetate as eluent gave (S)-methyl-2-phenylthiopropionate as a clear yellow oil (0.511 g, 2.60 mmol, 49%). $[α]_D=-165.4°$ (c=1.2, MeOH). $^1H$ NMR δ7.43 (m, 2H), 7.29 (m, 3H), 3.78 (q, 1H, J =7.12 Hz), 3.65 (s, 3H)), 1.47 (d, 3H, J=7.12 Hz); $^{13}C$ NMR δ172.87, 133.15, 133.01, 128.92, 128.00, 52.11, 45.07, 17.43.

EXAMPLE 16

(R)-Methyl-2-hexylthiophenylacetate (S)-Methyl mandelate (0.704 g, 4.24 mmol) in 9 ml of $CH_3CN$ was subjected to the reaction sequence of Example 5. Triflic anhydride (0.82 ml, 4.87 mmol) and 2,6-lutidine (0.57 ml, 4.87 mmol) were added and the triflate displaced with hexanethiol (0.82 ml, 5.51 mmol) and TEA (1.54 ml, 11.0 mmol). This reaction was stirred at −5° C. for 48 hours. The workup described in Example 5 and silica gel chromatography purification using 10 to 1 hexanes to ethyl acetate as the eluent, provided (R)-methyl-2-hexylthio-phenylacetate (0.73 g, 2.74 mmol, 65%) as a clear oil. $[α]_D=-2.6°$ (c=1.2, MeOH). $^1H$ NMR δ7.45 (m, 2H), 7.30 (m, 3H), 4.57 (s, 1H), 3.72 (s, 3H), 2.49 (m, 2H), 1.58–1.15 (m, 8H), 0.85 (t, 3H, J= 7.02); $^{13}C$ NMR δ171.14, 128.30, 127.97, 127.86, 52.28, 51.95, 31.75, 31.16, 28.29, 22.31, 13.79.

EXAMPLE 17

(S)-Methyl-2-hexylthiophenylacetate (R)-Methyl mandelate (0.657 g, 3.96 mmol) in 8 ml of $CH_3CN$ was subjected to the same reaction sequence of Example 5. Triflic anhydride (0.77 ml, 4.55 mmol) and TEA (0.63 ml, 4.55 mmol) were added, followed by hexanethiol (0.76 ml, 5.15 mmol) and TEA (0.72 ml, 5.15 mmol). The reaction was stirred at −5° C. for over 48 hours. Following the workup described in Example 5 and purification by silica gel chromatography using 25 to 1 hexane to ethyl acetate as eluent, (S)-methyl-2-hexylthiophenylacetate (0.501 g, 1.88 mmol, 48%) was isolated as a clear oil. $[\alpha]_D=+3.3°$ (c=1, MeOH). HRMS Calcd. for $C_{15}H_{14}O_2S$, 266.1346: Found: 266.1343.

EXAMPLE 18

(S)-2-Hexylthiodecanoic acid

To a 12 L flask equipped with a condenser and overhead stirrer was added (S)-methyl-2-hexylthiodecanoate (302.5 g, 1.00 mol), and 3 L of dry acetonitrile. To this solution was added sodium iodide (600 g, 4.00 mol) and iodine (25.4 g, 0.10 mol) followed by chlorotrimethylsilane (543 g, 635 ml, 5.00 mol). The reaction was heated to an internal temperature of 55° C. After 12 hours, an additional portion of chlorotrimethylsilane (130 g, 152 mL, 1.20 mol) was added and heating continued for 8 hours. The reaction was cooled to 0° C., 6 L of hexane was added followed by 1 L of ice water, and the layers were allowed to separate. The top hexane layer was separated and set aside. The combined $CH_3CN$/water layers were extracted with hexane (2×6 L). The combined hexane layers were washed with 1 L of water, 0.1M $Na_2S_2O_3$ (2×3 L) and once with 3 L of 1:1 brine/water. The combined hexane extracts were dried with $MgSO_4$, filtered and concentrated to give (S)-2-hexylthiodecanoic acid (260 g, 0.90 mol, 90%) as a colorless oil: $[\alpha]_D=-59.40°$ (C=1, MeOH); $^1H$ NMR δ3.19 (m, 1H), 2.63 (m, 2H), 1.95–1.18 (m, 22H), 0.95 (m, 6H).

(S)-2-hexylthiodecanoic acid was purified by formation of the dicyclohexylamine salt. (2S)-2-hexylthiodecanoic acid (0.30 gm, 1.05 mmol) was dissolved in 5 ml of $CH_3CN$ and to this solution was added dicyclohexyl amine (0.19 gm, 1.05 mmol) at rt. After stirring for 1 hour the salts were collected by filtration and recrystallized in 5–10 ml of $CH_3CN$. Dicyclohexyl ammonium (S)-2-hexylthiodecanoate was collected by filtration (0.420 gm, 0.89 mmol, 85%). Mp 84°–85° C. The salt was cleaved by stirring in 1N HCl and hexane for 1 hour. The (2S)-2-hexylthiodecanoic acid was recovered by extraction as above.

Alternatively, (S)-Methyl-2-hexylthiodecanoate (5.092 g, 16.8 mmol) was dissolved in methylene chloride (51 mL). To this solution was added hexamethyldisilane (5.4 mL, 26.4 mmol) and iodine (8.97 g, 35.3 mmol). The reaction was heated to 55° C. slowly and allowed to reflux for 2 hours. The reaction was cooled to rt and extracted with ethyl acetate (200 mL). The organic phase was washed with $H_2O$ (100 mL) followed by 0.1 N sodium bisulfite solution (2×200 mL) and brine. The organic phase was dried ($MgSO_4$) and concentrated to yield (S)-2-hexylthiodecanoic acid (4.66 g, 16.15 mmol, 96%). $[\alpha]_D=-49.7°$ (c=1.0, MeOH).

Alternatively, (S)-Methyl-2-hexylthiodecanoate (0.424 g, 1.40 mmol) was dissolved in acetonitrile (6 mL). To this solution was added hexamethyldisilane (0.29 mL, 1.42 mmol) and iodine (0.36 g, 1.42 mmol). The reaction was heated to 55° C. slowly and allowed to reflux for 6 hours. An additional set of equivalents of hexamethyldisilane and iodine were added and the reaction continued for 20 hours. The reaction was quenched by the addition of $H_2O$ (6 mL) and extracted with hexane (2×40 mL). The organic phase was washed with 0.1N sodium bisulfite solution and brine. It was dried ($MgSO_4$) and concentrated to (S)-2-hexylthiodecanoic acid (0.354 g, 1.22 mmol, 88%).

EXAMPLE 19

(2S)-N-(6-Methylthioquinolin-5-yl)-2-hexylthio-decanoamide (S)-2-hexylthiodecanoic acid (Example 18) (0.89 g, 3.08 mmol) was dissolved in 15 ml of methylene chloride and cooled to 0° C. A catalytic amount of dimethylformamide (DMF) (0.012 ml, 0.15 mmol) was added followed by oxalyl chloride (0.32 ml, 3.70 mmol). The reaction was allowed to warm to rt and stirred for 1–1.5 hours. N-6-Methylthio-5-quinolinamine (0.616 g, 3.24 mmol) was dissolved in 2 ml of pyridine and added dropwise to the reaction. The reaction was stirred at rt for 3 hours. Ethyl acetate (35 ml) was added and the organic phase was washed with saturated $NaHCO_3$ (2×10 ml) followed by water (2×10 ml). The ethyl acetate extracts were dried and concentrated to give crude (S)-N-(6-methylthio-quinolin-5-yl)-2-hexylthiodecanoamide (2.22 g recovered). (S)-N-(6-Methylthioquinolin-5-yl)-2-hexylthiodecanoamide was recrystallized from acetonitrile (6 ml), to give the pure title compound (1.02 g, 2.2 mmol, 72%) as a white solid: mp 113.5°–114.5°; $[\alpha]_D=-73.0°$ (c=0.7, MeOH); $[\alpha]_D=-51.6°$ (C=0.5, $CHCl_3$); IR ($CHCl_3$) 3652, 3304, 2921, 2851, 1674, 1584, 1566, 1468, 1376, 1311, 1170, 969, 866, 823 $cm^{-1}$; $^{13}C$ NMR 171.96, 149.75, 146.71, 134.26, 131.36, 129.51, 128.99, 126.89, 125.63, 121.69, 51.08, 33.08, 32.27, 31.87, 31.43, 29.42, 29.30, 29.25, 28.65, 27.78, 22.68, 22.55, 15.73, 14.12, 14.03. Anal. Calcd for $C_{26}H_{40}N_2OS_2$: C, 67.78; H, 8.75; N, 6.08: Found C, 67.71; H, 8.82; N, 6.03%

$^1H$ NMR 8.84 (dd, 1H, J=2.5, 4.2 Hz), 8.61 (s, 1H), 8.04 (t, 2H), J=8.87 Hz), 7.66 (d, 1H, J=8.7 Hz), 7.39 (dd, 1H, J=8.5, 8.7 Hz) 3.52 (dd, 1H, J=6.2, 8.1 Hz) 2.79 (t, 2H, J=7.3 Hz), 2.55 (s, 3H), 2.12 (m, 1H), 1.85 (m, 1H), 1.65–1.29 (m, 20H), 0.85 (m, 6H).

EXAMPLE 20

(2S)-N-2,4-[(methylthio)-6-methyl-3-pyridinyl]-2-hexylthiodecanoamide

Following the procedure outlined in example 19, (S)-2-hexylthiodecanoic acid (5.30 g, 18.4 mmol) was coupled via the acid chloride to N-2,4-(methylthio)-6-methyl-3-pyridineamine (4.61 g, 23 mmol) to produce (2S)-N-2,4-[(methylthio)-6-methyl-3-pyridinyl]-2-hexylthiodecanoamide (8.50 g. 18.05 mmol, 98%) as an off-white solid. This material was judged to be 93% ee.

EXAMPLE 21

(2S)-N-(6-Methylthioquinolin-5-yl)-2-hexylthio-decanoamide

N-6-Methylthio-5-quinolinamine (0.61 g, 3.23 mmol) was dissolved in 20 ml of methylene chloride. A solution of $AlMe_3$ (3.23 ml, 6.46 mmol of 2.0M solution in hexane) was added dropwise. The reaction mixture turned bright red and was stirred at rt for 20 minutes. (S)-methyl-2-hexylthiodecanoate was added in 10 ml of methylene chloride and the reaction heated to a bath temperature of 55° C. After 20 hours, the reaction was cooled, poured into a saturated aqueous solution of $NaHCO_3$ and extracted with ethyl acetate (2×60 ml). The organic phase was washed with NaHCO$_3$ followed by brine, dried over MgSO$_4$ and concentrated to give yellow solids (1.50 gm, 3.25 mmol, 100%). The solids were recrystallized from 10 ml of acetonitrile to yield (2S)-N-(6-methylthioquinolin-5-yl)-2-hexylthiodecanoamide as a white solid (0.58 gm, 1.26 mmol, 39%). [α]$_D$=−51.74° (c=0.31, CHCl$_3$); Mp 101°–102° C.; Exact mass (EI) calculated for C$_{26}$H$_{40}$N$_2$S$_2$O: 460.2573, found 460.2575.

EXAMPLE 22

(2S)-N-2,4[(Methylthio)-6-methyl-3-pyridinyl]-2-phenylthiodecanoamide.

N-2,4-(Methylthio)-6-methyl-3-pyridinamine (0.117 gm, 0.58 mmol) was dissolved in 3 ml of methylene chloride and treated with AlMe$_3$ (0.65 ml, 1.28 mmol of 2.0M solution in hexane). This solution was heated to a bath temperature of 50°–55° C. and stirred for 1–1.5 hours. Methyl 2-phenylthiodecanoate was added to the reaction in 1 ml of methylene chloride. Heating was continued for 5 hours; then the reaction was allowed to stir at rt for 48 hours. The reaction was slowly poured into saturated NaHCO$_3$ (5 ml) and extracted with ethyl acetate (2×10 ml). The combined organic layers were washed with NaHCO$_3$ (2×5 ml), brined and dried over MgSO$_4$. Following concentration of the solvent, the crude oil was recrystallized from 1.5 ml of acetonitrile to give (2S)-N-2,4-[(Methylthio)-6-methyl-3-pyridinyl] 2-phenylthiodecanamide (0.104 gm, 0.22 mmol, 39%) as a white solid. Mp 102°–104° C. $^1$H NMR δ7.97 (s, 1H), 7.46 (m, 2H), 7.26 (m, 3H), 6.59 (s, 1H), 3.91 (dd, 1H, J=6.1, 8.1 Hz), 2.46 (s, 3H), 2.45 (s, 3H), 2.31 (s, 3H), 2.16 (m, 1H), 1.93 (m, 1H), 1.64 (m, 2H), 1.26 (m, 10H), 0.86 (t, 3H, J=6.7 Hz).

EXAMPLE 23

(2R)-N-(6-Methylthioquinolin-5-yl)-2-hydroxydecanoamide (R)-2-Hydroxydecanoic acid (2.3 gm, 12.24 mmol) was dissolved in 70 ml of methylene chloride and chlorotrimethylsilane TMSCI (3.42 ml, 26.9 mmol) and catalytic DMAP were added to the reaction. Pyridine (2.18 ml, 26.9 mmol) was added slowly and the reaction stirred at rt for 12 hours. The reaction was cooled to 0° C. and 0.4 ml of DMF added followed by oxalyl chloride (1.28 ml, 14.67 mmol). The reaction was allowed to warm slowly to rt over 1.5 hours. The amine (2.33 gm, 12.24 mmol) was dissolved in 15 ml of pyridine and added to the reaction. Stirring was continued at rt for 6 hours. The reaction was poured into a saturated solution of NaHCO$_3$ (50 ml) and extracted with ethyl acetate (2×100 ml). The organic layers were washed with saturated NaHCO$_3$ (2×50 ml) and brine. The combined ethyl acetate layers were dried (MgSO$_4$) and concentrated to give an orange oil (6 gm). This material was dissolved in 75 ml of THF at rt and nBu$_4$NF-3H$_2$O (4.64 gm, 14.7 mmol) added and the reaction stirred for 4 hours. The reaction was poured into saturated NaHCO$_3$ (50 ml) and extracted with ethyl acetate (2×100 ml). The organic phase was washed with brine, dried (MgSO$_4$) and concentrated to a waxy solid (6 gm). The solid was recrystallized from ethyl acetate (50 ml) to give(2R)-N-(6-methylthioquinolin-5-yl)-2-hydroxydecanoamide (3.53 gm, 9.79 mmol, 80%) as a height solid. [α]$_D$=+33.49° (c=0.41, MeOH); Mp 119°–120° C.

EXAMPLE 24

(2S)-N-(6-Methylthioquinolin-5-yl)-hexylthiodecanoamide (2R)-N-(6-Methylthioquinolin-5-yl)-2-hydroxydecanoamide (0.55 gm, 1.5 mmol) was dissolved in 10 ml of methylene chloride, cooled to 0° C. and treated with catalytic DMAP followed by TEA (0.25 ml, 1.8 mmol) and MsCl (0.14 ml, 1.8 mmol). The reaction was stirred for 2 hours and then poured into saturated NaHCO$_3$ (5 ml) and extracted with ethyl acetate (10 ml). The organic layer was washed with brine, dried (MgSO$_4$) and concentrated to a foam. The material was purified by silica gel chromatography using 80% ethyl acetate to hexane as the eluent. (2R)-N-(6-Methylthioquinolin-5-yl)-2-methanesulfonate decanoamide was obtained (0.341 gm, 0.78 mmol, 52%). $^1$H NMR δ8.68 (d, 1H, J=2.8 Hz), 8.54 (s, 1H), 7.95 (d, 1H, J=8.4 Hz), 7.82 (d, 1H, J=9.0 Hz), 7.32 (d, 1H, J=9.0 Hz), 7.21 (m, 1H),, 5.11 (t, 1H, J=6.6 Hz), 3.05 (s, 3H), 2.33 (s, 3H), 1.97–1.21 (m, 14H), 0.83 (t, 3H, J=6.63 Hz).

Hexanethiol (0.077 ml, 0.54 mmol) was dissolved in 2 ml of THF and treated with KOtBu (0.025 gm, 0.22 mmol) and the reaction stirred at rt for 30 minutes. To the solution was added (2R)-N-(6-methylthioquinolin-5-yl)-2-methanesulfonatedecanoamide (0.08 gm, 0.18 mmol) in 1 ml of THF and the reaction stirred at rt for 1 hour. The reaction was poured into saturated NaHCO$_3$ (5 ml) and extracted with ethyl acetate (2×10 ml). The organic layer was washed with brine, dried (MgSO$_4$) and concentrated to give (2S)-N-(6-methylthioquinolin-5-yl)-2-hexylthiodecanoamide as a white solid (0.68 gm, 0.147 mmol, 82%). [α ]$_D$=−17.74° (c=0.45, MeOH); Mp 86°–88° C.

EXAMPLE 25

(2S)-N-(6-Methylthioquinolin-5-yl)-2-phenylthiodecanoamide

Thiophenol (0.15 ml, 1.46 mmol) was dissolved in 5 ml of THF and cooled to 0° C. To this solution was added potassium t-butoxide (KOtBu) (0.084 gm, 0.75 mmol) and the slurry was stirred for 30 minutes. (2R)-N-(6-Methylthioquinolin-5-yl)-2-methanesulfonatedecanoamide (0.218 gm, 0.49 mmol) was dissolved in 2 ml of THF and added to the thiol solution. The reaction was allowed to slowly warm to rt and stirred for 2 hours. The reaction was poured into saturated NaHCO$_3$ and extracted with ethyl acetate. The organic layer was washed with brine, dried and concentrated to a crude oil. The oil was purified by silica gel chromatography using 50% hexane/ethyl acetate as the eluent to yield (2S)-N-(6-methylthioquinolin-5-yl)-2-phenylthiodecanoamide as a white solid (0.14 gm, 0.31 mmol, 63%). Mp 126°–128° C. [α]$_D$=−132.0° (c=0.80, MeOH).

EXAMPLE 26

(2S)-N-(6-Methylthioquinolin-5-yl)-2-phenylthiodecanoamide (2R)-N-(6-Methylthioquinolin-5yl)-2-methanesulfonatedecanoamide (0.29 gm, 0.66 mmol) and thiophenyl (0.13 ml, 1.26 mmol) were dissolved in 6 ml of acetonitrile. To this solution was added tetramethyl guanidine (0.091 ml, 0.73 mmol) and the reaction stirred at rt for 2 hours. The reaction was poured into NaHCO$_3$ (5 ml) and extracted with ethyl acetate (2×10 ml). The organic layers were washed with brine, dried (MgSO$_4$) and concentrated to yield a crude solid that was crystallized from 10 ml of acetonitrile to give (2S)-N-(6-methylthioquinolin-5-yl)-2-phenylthiodecanoamide as a white solid (0.168 gm, 0.37 mmol, 56%). Mp 128°–129° C. $[\alpha]_D=-108.3°$ (C=0.30, MeOH). HRMS calc'd for $C_{26}H_{32}ON_2S_2$, 452.1949; found, 452.1970.

EXAMPLE 27

(2R)-N-2,4-[(Methylthio)-6-methyl-3-pyridinyl]-2-hydroxydecanoamide

Following the procedure of Example 23, (R)-2-hydroxydecanoic acid (0.966 gm, 5.13 mmol) was coupled to N-2,4-(methylthio)-6-methyl-3-pyridinamine (1.03 gm, 5.14 mmol) to yield (2R)-N-[2,4-(methylthio)-6-methyl-3-pyridinyl]-2-hydroxydecanoamide (1.47 gm, 3.96 mmol, 77%) as a beige solid. Mp 97°–98° C. $[\alpha]_D=+28.6°$ (c=0.50 MeOH).

EXAMPLE 28

(2S)-N-2,4[(Methylthio)-methyl-3-pyridinyl]-2-hexylthiodecanoamide

Following the procedure of Example 24, (2R)-N-[2,4-(methylthio)-6-methyl-3-pyridinyl]-2-hydroxydecanoamide (0.262 gm, 0.707 mmol) was converted to (2R)-N-[2,4-(methylthio)-6-methyl-3-pyridinyl]-2-methanesulfonatedecanoamide (0.34 gm, 0.70 mmol, 98%) as a white solid. $^1$H NMR δ7.41 (s, 1H), 6.68 (s, 1H), 5.16 (t, 2H, J=8.1 Hz), 3.20 (s, 3H), 2.51 (s, 3H), 2.49 (s, 3H), 2.2–0.85 (m, 17H).

Hexanethiol (0.13, 0.92 mmol) was dissolved in 3 ml of tetrahydrofuran (THF). Potassium t-butoxide (0.66 g, 0.58 mmol) was added at rt and the reaction stirred for 30 minutes. (2R)-N-[2,4-(Methylthio)-6-methyl-3-pyridinyl]-2-methanesulfonatedecanoamide (0.222 g, 0.45 mmol) was dissolved in 1 ml of THF and added to the reaction at rt. Stirring was continued for 2 hours. The reaction was poured into 10 ml of saturated NaHCO$_3$ and extracted with 15 ml of ethyl acetate. The organic phase was washed with brine, dried (MgSO$_4$) and concentrated to solids. The solids were recrystallized from 1 ml of CH$_3$CN to produce (2S)N-2,4-[(Methylthio)-6-methyl-3-pyridinyl]2-hexylthiodecanoamideas a white solid: (0.055 g, 0.12 mmol, 26%), $[\alpha]_D=+41.18°$ (c=0.76, MeOH); Mp 73°–76° C.

EXAMPLE 29

(2S)-N-2,4[(Methylthio)-methyl-3-pyridinyl]-2-phenylthiodecanoamide

Following the procedure in Example 24, (2R)-N-2,4[(methylthio)-methyl-3-pyridinyl]-2-hydroxydecanamide (0.21 g, 0.566 mmol) was converted to (2R)-N-2,4[(methylthio)-methyl-3-pyrindinyl]-2 -methanesulfonatedecanamide. Following the procedure in Example 24, this material was directly converted to (2S)-N-2,4[(Methylthio)-methyl-3-pyridinyl]-2-phenylthiodecanamide (0.149 g, 0.322 mmol, 57%). $[\alpha]_D=-89.26°$ (c=0.81, MeOH); MP 97°–98.5° C.

EXAMPLE 30

(S)-(−)-2-Bromodecanoic acid (S)-2-Aminodecanoic acid from Takasago Research Institute (1.5 g., 8.0 mmol) and potassium bromide (3.8 g, 32 mmol) were dissolved in 16 ml of 2.5 m H$_2$SO$_4$ (40 mmol). Slight heating was necessary to the make the reaction homogeneous. The solution was cooled to 0° C. and sodium nitrite (1.1 g, 16 mmol) dissolved in 2 ml water was added dropwise. Brown gas evolved and foaming occurred. The reaction was stirred at 0° C. for 30 minutes and at rt for 2 hours. The reaction was quenched with 100 ml of 5% sodium thiosulfate and extracted with ethyl acetate (3×100 ml). The concentrated organic phase was purified by silica gel column chromatography (eluent: 100% CH$_2$Cl$_2$) to yield 1.2 g (61% yield) of the desired product: $[\alpha]^{20}D=-29.9°$ (c=0.032, MeOH); $^1$H NMR (CDCl$_3$ δ10.28 (1H, br s), 4.22 (1H, t, J=7.4 Hz), 2.02 (2H, m), 1.26 (12H, m), 0.87 (3H, t, J=6.8 Hz).

EXAMPLE 31

(R)-2-Bromodecanoic acid

Using the procedure outlined in Example 30, (R)-2-aminodecanoic acid (45.0 g, 290 mmol, Takasago Research Institute) was converted to (R)-2-bromodecanoic acid (48.1 g, 191 mmol, 66%). $[\alpha]_D=+29.0°$ (c=1.0, MeOH).

EXAMPLE 32

(R)-(+)-2-Hexylthiodecanoic acid (S)-(−)-2-Bromodecanoic acid (250 mg, 1 mmol) and cesium carbonate (980 mg, 3 mmol) were mixed in 5 ml THF and cooled to 0° C. The reaction was not homogeneous. Hexanethiol was added dropwise. The reaction was allowed to warm to rt and stirred under N$_2$ for 18 hours. The reaction was quenched with 100 ml 1N HCl and extracted with ethyl acetate (3×50 ml). The concentrated organic phase was purified by silica gel column chromatography (eluent: 100% CH$_2$Cl$_2$) to yield 230 mg (80% yield) of the desired product: $[\alpha]^{20}_D=+57.9$ (c=0.022, MeOH); $^1$H NMR (CDCl$_3$) δ3.21 (1H, dd, J =6.9, 7.0 Hz), 2.62 (2H, m), 1.84 (1H, m), 1.58 (2H, m), 1.26 (19H, m), 0.87 (6H, m).

EXAMPLE 33

(R)-(+)-2-Hexylthiodecanoic acid (S)-(−)-2-Bromodecanoic acid (125 mg, 0.50 mmol, $[\alpha]^{20}_D=-29,9°$ in MeOH) and potassium tert-butoxide (200 mg, 1.8 mmol) were mixed in 3 ml THF and cooled to 0° C. The reaction was not homogeneous. Hexanethiol (84 mg, 0.71 mmol) was added dropwise. The reaction was allowed to warm to rt and stirred under N$_2$ for 18 hours. The reaction was quenched with 100 ml 1N HCl and extracted with ethyl acetate (3×50 ml). The concentrated organic phase was purified by silica gel column chromatography (eluent: 100% CH$_2$Cl$_2$) to yield 52 mg (36% yield) of the desired product: $[\alpha]^{20}_D=+56.0°$ (c=0.015, MeOH); $^1$H NMR (CDCl$_3$) δ3.22 (1H, dd, J=7.7, 7.3 Hz), 2.62 (2H, m), 1.85 (1H, m), 1.58 (2H, m), 1.25 (19H, m), 0.87 (6H, m).

EXAMPLE 34

(S)-2-Hexylthiodecanoic acid

Using the procedure outlined in Example 33, (R)-2-bromodecanoic acid (0.374 g, 1.49 mmol) was treated with potassium tert-butoxide (0.480 g, 4.28 mmol) in THF (9 mL) at 0° C. Hexanethiol (0.30 mL, 2.02 mmol) was added dropwise and the reaction was stirred for 18 hours. The reaction was poured into 1N HCl (25 mL) and extracted with hexane (2×25 mL). The combined organic layers were washed with NaHCO$_3$ solution (25 mL, 0.5M), followed by HCl (1N, 25 mL) and dried (MgSO$_4$). Following solvent removal, (S)-hexylthiodecanoic acid (0.34 g, 1.18 mmol, 80%) was obtained. This material was judged to be 95% ee.

Following the procedure outlined above, (R)-2-bromodecanoic acid (0.50 g, 2.0 mmol) was treated with tetramethylguanidine (0.63 mL, 5.0 mmol) and hexanethiol (0.90 mL, 6.0 mmol) in acetonitrile (5 mL). After the workup described above, (S)-hexylthiodecanoic acid (0.75 g, 2.59 mmol) was obtained as a yellow oil. This material was judged to be 95% ee.

Following the procedure outlined above, (R)-2-bromodecanoic acid (0.505 g, 2.01 mmol) was treated with cesium carbonate (1.64 g, 5.03 mmol) in DMF (8 mL). To this mixture was added hexanethiol (0.9 mL, 6.0 mmol) and the reaction stirred for 2 hours. Following the workup outlined above, (S)-2-hexylthiodecanoic acid (0.573 g, 1.98 mmol, 99%) was obtained as a yellow oil. This material was judged to be greater than 96% ee.

Following the procedure outlined above, (R)-2-bromodecanoic acid (0.514 g, 2.05 mmol) was treated with potassium carbonate (0.69 g, 5.0 mmol) in DMF (8 mL). To this mixture was added hexanethiol (0.9 mL, 6.0 mmol) and the reaction heated to 60° C. for 10 hours. Following the workup outlined above, (S)-2-hexylthiodecanoic acid (0.52 g, 1.80 mmol, 88%) was obtained as a cloudy oil.

EXAMPLE 35

(S)-2-hexylthiodecanoic acid

Following the procedure outlined in Example 34 (R)-2-bromodecanoic acid (0.514 g, 2.05 mmol) was dissolved in THF (10 mL) and cooled to 0° C. Potassium hydroxide (0.396 g, 6.16 mmol) was added and after 15 minutes was followed by the addition of hexanethiol (0.91 mL, 6.15 mmol). The reaction was allowed to slowly come to room temperature and stir for 18 hours. Following the workup outlined above, (S)-2-hexylthiodecanoic acid (0.533 g, 1.85 mmol, 90%) was obtained as a pale yellow oil. This material was judged to be greater than 93% ee.

EXAMPLE 36

(R)-(+)-2-Phenylthiodecanoic acid (S)-(−)-2-Bromodecanoic acid (250 mg, 1.0 mmol, $[\alpha]^{20}_D=-29.9°$ in MeOH) and cesium carbonate (980 mg, 3.0 mmol) were mixed in 5 ml THF and cooled to 0° C. The reaction was not homogeneous. Thiophenol (120 mg, 1.1 mmol) was added dropwise. The reaction was allowed to warm to rt and stirred under $N_2$ for 18 hours. The reaction was quenched with 100 ml 1N HCl and extracted with ethyl acetate (3×50 ml). The concentrated organic phase was purified by silica gel column chromatography (eluent: 100% $CH_2Cl_2$) to yield 235 mg (84% yield) of the desired product: $[\alpha]^{20}_D=+70.5°$ (c=0.036, MeOH); $^1$H NMR (CDCl$_3$) δ7.45 (2H, m), 7.29 (3H, m), 3.61 (1H, t, J=7.7, 7.3 Hz), 1.87 (1H, m), 1.76 (1H, m), 1.44 (2H, m), 1.25 (10H, bs), 0.87 (3H, t, J=6.0, 7.0 Hz).

EXAMPLE 37

N-(6-Methylthioquinolin-5-yl)-2-(hexylthio)-decanoic amide (R)-N-(6-Methylthioquinolin-5-yl)-2-bromodecanoic amide (43 mg, 0.10 mmol) in 1 ml of DMF was cooled to 0° C. To this was added a cooled suspension of NaH (9 mg, 0.38 mmol) and hexanethiol (67 mg, 0.57 mmol) in 1 ml DMF. The reaction was allowed to warm to rt over a period of 12 hours and quenched with 5 ml of saturated NH$_4$Cl. The aqueous layer was extracted with ethyl acetate (3×10 ml). Purification of the organic phase by silica gel column chromatography (eluent: 100% CHCl$_3$) yielded 30 mg (65% yield) of the desired product. $^1$H NMR (CDCl$_3$) δ8.85 (1H, d, J=3 Hz), 8.62 (1H, s), 8.05 (3H, d, J=9 Hz), 8.00 (1H, d, J=9 Hz), 7.65 (1H, d, J=9 Hz), 7.40 (1H, dd, J=9, 9 Hz), 3.55 (1H, t, J=8 Hz), 2.80 (2H, t, J=8 Hz), 2.50 (3H, s), 2.20–1.30 (22H, m), 0.91 (6H, t, J=9 Hz).

EXAMPLE 38

N-(6-Methylthioquinolin-5-yl)-2-(hexylthio)-decanoic amide (S)-N-(6-Methylthioquinolin-5-yl)-2-bromodecanoic amide (39 mg, 0.09 mmol) in 1 ml of dry THF was added slowly to a suspension containing cesium carbonate (67 mg, 0.20 mmol) and hexanethiol (13 mg, 0.11 mmol) in 2 ml of THF. After 18 hours, the reaction was quenched with 2 ml of 1N HCl and extracted with ethyl acetate (4×10 ml). The organic phase was purified by silica gel column chromatography (eluent: 100% CHCl$_3$) to yield 25 mg (60% yield) of the desired product. $^1$H NMR (CDCl$_3$) δ8.85 (1H, d, J=3 Hz), 8.62 (1H, s), 8.05 (1H, d, J=9 Hz), 8.00 (1H, d, J=9 Hz), 7.65 (1H, d, J=9 Hz), 7.40 (1H, dd, J=9, 9 Hz), 3.55 (1H, t, J=8 Hz), 2.80 (2H, t, J=8 Hz), 2.50 (3H, s), 2.20–1.30 (22H, m), 0.91 (6H, t, J=Hz).

EXAMPLE 39

(R)-N-(6-Methylthioquinolin-5-yl)-2-bromodecanoic amide (R)-2-Bromodecanoic acid (210 mg, 0.83 mmol), 5-amino-6-methylthioquinoline (160 mg, 0.84 mmol) and 2-ethoxy-1-ethoxycarbonyl-1,2-dihydroquinoline (EEDQ, 223 mg, 0.90 mmol) were stirred in 6 ml of toluene at 0° C. The reaction was allowed to warm to rt and stirred under $N_2$ for 18 hours. The reaction was quenched with 100 ml of 10% citric acid and extracted with ethyl acetate (3×50 ml). The organic phase was washed with 0.5N NaHCO$_3$, brined and dried over Na$_2$SO$_4$. Purification by silica gel column chromatography (eluent: 100% CHCl$_3$) yielded 120 mg (34% yield) of the desired product: $^1$H NMR (CDCl$_3$) δ8.85 (1H, d, J=3 Hz), 8.09 (1H, d, J=9 Hz), 8.08 (1H, d, J=9 Hz), 7.98 (1H, bs), 7.65 (1H, d, J=9 Hz), 7.42 (1H, dd, J=9, 9 Hz), 4.61 (1H, dd, J=8, 8 Hz), 2.58 (3H, s), 2.33 (1H, m), 2.21 (1H, m), 1.76–121 (12H, m), 0.88 (3H, m).

We claim:

1. A process of preparing (S)-methyl-2-hexylthiodecanoate or (R)-methyl-2-hexylthiodecanoate, comprising: (a) reacting (S)-methyl-2-hydroxydecanoate or (R)-methyl-2-hydroxydecanoate, respectively, with methanesulfonic acid, diisopropyl azodicarboxylate, triphenylphosphine, and a base to form (R)-methyl-2-methanesulfonatedecanoate or (S)-methyl-2-methanesulfonatedecanoate, respectively; and (b) reacting the (R)-methyl-2-methanesulfonate-decanoate or (S)-methyl-2-methanesulfonate-decanoate so formed with hexanethiol in the presence of a base.

2. A process of preparing either (R)-methylbenzylammonium-(2R)-hydroxydecanoate and (R)-methylbenzylammonium-(2S)-hydroxydecanoate, or (S)-methylbenzylammonium-(2R)-hydroxydecanoate and (S)-methylbenzylammonium-(2S)-hydroxydecanoate, comprising reacting (R)-(+)-α-methyl-benzylamine or S-(−)-α-methylbenzylamine, respectively, with 2-hydroxydecanoic acid.

3. A process of preparing (S)-(−)-2-bromodecanoic acid or (R)-(+)-2-bromodecanoic acid comprising reacting, respectively, (S)-2-aminodecanoic acid or (R)-2-aminodecanoic acid with sodium or potassium nitrite and an alkali or alkaline earth metal bromide in the presence of an acid.

4. A compound of the formula

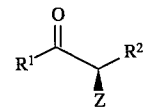

(II-A)

-continued

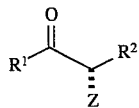
(II-A')

wherein $R^1$ is selected from the group consisting of hydroxy, $(C_1-C_6)$alkoxy and benzyloxy wherein the benzyl moiety may optionally be substituted with from one to three substituents independently selected from the group consisting of $(C_1-C_6)$alkyl, $(C_1-C_6)$alkoxy, $(C_1-C_6)$alkylthio, halo, nitro and trifluoromethyl, or $R^1$ is $NHR^5$ wherein $R^5$ is

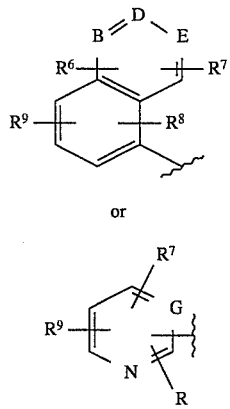

wherein B, D, E and G are independently carbon or nitrogen with the proviso that at least one of B, D and E is nitrogen, $R^6$, $R^7$, $R^8$ and $R^9$ are each independently selected from the group consisting of hydrogen, $(C_1-C_6)$alkyl, $(C_1-C_6)$alkoxy, $(C_1-C_6)$alkylthio, $(C_5-C_7)$cycloalkylthio and $NR^{10}R^{11}$, wherein $R^{10}$ and $R^{11}$ are independently selected from the group consisting of hydrogen and $(C_1-C_6)$alkyl, and wherein $R^6$, $R^7$, $R^8$ and $R^9$, when attached to a bicyclic system of formula A, may be attached to either ring of such system, with the proviso that no more than 3 non-hydrogen, substituents may be attached to any one ring of such system; $R^2$ is a hydrocarbon containing 6 to 12 carbons; and Z is (a) chloro, bromo or iodo when $R^1$ is hydroxy, (b) $OSO_2R^3$ wherein $R^3$ is $(C_1-C_7)$alkyl, trifluoromethyl or phenyl optionally substituted with $(C_1-C_7)$alkyl, chloro, fluoro, bromo, iodo or nitro, when $R^1$ is $(C_1-C_6)$alkoxy or benzyloxy, and (c) chloro, fluoro, bromo, iodo, $OSO_2R^3$ or hydroxy when $R^1$ is $NHR^5$.

5. A diasteriomeric salt of a decanoic acid containing an asymmetric center alpha to a carbonyl moiety wherein said diasteriomeric salt is selected from:
   (R)-Methylbenzylammonium-(2R)-hydroxydecanoate,
   (R)-Methylbenzylammonium-(2S)-hydroxydecanoate,
   (S)-Methylbenzylammonium-(2R)-hydroxydecanoate,
   (S)-Methylbenzylammonium-(2S)-hydroxydecanoate,
   Dicyclohexylammonium-(S)-2-hexylthiodecanoate,
   and Dicyclohexylammonium-(R)-2-hexylthiodecanoate.

6. A process of preparing (S)-methyl-2-hexylthio-decanoate or (R)-methyl-2-hexylthiodecanoate, comprising: (a) reacting (R)-methyl-2-hydroxydecanoate or (2S)-methyl-2-hydroxydecanoate, hydroxydecanoate, respectively, with trifluoromethane sulfonic anhydride (triflic anhydride) in the presence of a base to form (R)-methyl-2-trifluoromethanesulfonate-decanoate or (S)-methyl-2-trifluoromethanesulfonate-decanoate, respectively; and (b) reacting the (R)-methyl-2-trifluoromethanesulfonatedecanoate or (S)-methyl-2-trifluoromethanesulfonatedecanoate so formed with hexanethiol in the presence of a base.

* * * * *